United States Patent
Kamiguchi (10) Patent No.: US 10,381,195 B2
(45) Date of Patent: Aug. 13, 2019

(54) CHARGED PARTICLE BEAM TREATMENT APPARATUS

(71) Applicant: SUMITOMO HEAVY INDUSTRIES, LTD., Tokyo (JP)

(72) Inventor: Nagaaki Kamiguchi, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/653,861

(22) Filed: Jul. 19, 2017

(65) Prior Publication Data

US 2019/0027339 A1   Jan. 24, 2019

(51) Int. Cl.
| | |
|---|---|
| *H01J 37/30* | (2006.01) |
| *H01J 37/304* | (2006.01) |
| *A61N 5/10* | (2006.01) |
| *G21K 5/00* | (2006.01) |

(52) U.S. Cl.
CPC .......... *H01J 37/304* (2013.01); *A61N 5/1048* (2013.01); *G21K 5/00* (2013.01); *A61N 5/1043* (2013.01); *A61N 5/1065* (2013.01); *A61N 5/1077* (2013.01); *A61N 2005/1087* (2013.01)

(58) Field of Classification Search
CPC ... H01J 37/304; A61N 5/1048; A61N 5/1065; A61N 5/1067; A61N 5/1077; A61N 2005/1087
See application file for complete search history.

(56) References Cited

U.S. PATENT DOCUMENTS

| | | | |
|---|---|---|---|
| 6,265,837 B1 * | 7/2001 | Akiyama | A61N 5/1043 250/492.3 |
| 8,153,989 B2 | 4/2012 | Tachikawa et al. | |
| 2004/0227104 A1 * | 11/2004 | Matsuda | A61N 5/10 250/492.1 |
| 2009/0032527 A1 * | 2/2009 | Lee | A23L 3/28 219/679 |
| 2009/0189085 A1 * | 7/2009 | Rogers | A23L 3/263 250/455.11 |
| 2010/0001212 A1 * | 1/2010 | Nishiuchi | A61N 5/10 250/492.3 |
| 2010/0072389 A1 | 3/2010 | Tachikawa et al. | |

(Continued)

FOREIGN PATENT DOCUMENTS

JP   2009-243891 A   10/2009

*Primary Examiner* — David E Smith
(74) *Attorney, Agent, or Firm* — Michael Best & Friedrich LLP (57) ABSTRACT

A charged particle beam treatment apparatus includes an accelerator that emits a charged particle beam by accelerating a charged particle, an irradiation unit that irradiates an irradiation target body with the charged particle beam, a beam transport line that connects the accelerator and the irradiation unit to each other, and that transports the charged particle beam from the accelerator to the irradiation unit, and a control unit that controls the irradiation unit in irradiating the irradiation target body with the charged particle beam. The irradiation unit includes a scanning unit that scans each layer with the charged particle beam. After one layer is scanned with the charged particle beam by using a first current value, the control unit controls the irradiation unit so as to scan and irradiate the one layer with the charged particle beam by using a second current value which is different from the first current value.

3 Claims, 6 Drawing Sheets

(56) References Cited

U.S. PATENT DOCUMENTS

| 2013/0023716 A1* | 1/2013 | Thomas | A61N 5/1075 |
| | | | 600/1 |
| 2014/0018603 A1* | 1/2014 | Asaba | A61N 5/1031 |
| | | | 600/1 |
| 2015/0151140 A1* | 6/2015 | Hori | G01T 1/2935 |
| | | | 250/397 |

* cited by examiner

| 0 | 0 | 201 | 178 | 90 | 184 | 205 | 0 |
|---|---|---|---|---|---|---|---|
| 0 | 202 | 122 | 88 | 82 | 95 | 133 | 210 |
| 191 | 182 | 76 | 30 | 5 | 51 | 129 | 208 |
| 198 | 143 | 23 | 4 | 3 | 21 | 106 | 183 |
| 201 | 142 | 38 | 8 | 2 | 22 | 78 | 141 |
| 0 | 192 | 75 | 11 | 4 | 35 | 111 | 183 |
| 0 | 0 | 204 | 69 | 45 | 35 | 177 | 0 |
| 0 | 0 | 0 | 199 | 80 | 159 | 0 | 0 |

FIG. 4B

| 0 | 0 | 201 | 178 | 0 | 184 | 205 | 0 |
|---|---|---|---|---|---|---|---|
| 0 | 202 | 122 | 0 | 0 | 0 | 133 | 210 |
| 191 | 182 | 0 | 0 | 0 | 0 | 129 | 208 |
| 198 | 143 | 0 | 0 | 0 | 0 | 106 | 183 |
| 201 | 142 | 0 | 0 | 0 | 0 | 0 | 141 |
| 0 | 192 | 0 | 0 | 0 | 0 | 111 | 183 |
| 0 | 0 | 204 | 0 | 0 | 0 | 177 | 0 |
| 0 | 0 | 0 | 199 | 0 | 159 | 0 | 0 |

RANGE 1,000-100

FIG. 4C

| 0 | 0 | 0 | 0 | 90 | 0 | 0 | 0 |
|---|---|---|---|---|---|---|---|
| 0 | 0 | 0 | 88 | 82 | 95 | 0 | 0 |
| 0 | 0 | 76 | 30 | 0 | 51 | 0 | 0 |
| 0 | 0 | 23 | 0 | 0 | 21 | 0 | 0 |
| 0 | 0 | 38 | 0 | 0 | 22 | 78 | 0 |
| 0 | 0 | 75 | 11 | 0 | 35 | 0 | 0 |
| 0 | 0 | 0 | 69 | 45 | 35 | 0 | 0 |
| 0 | 0 | 0 | 0 | 80 | 0 | 0 | 0 |

RANGE 99-10

FIG. 4D

| 0 | 0 | 0 | 0 | 0 | 0 | 0 | 0 |
|---|---|---|---|---|---|---|---|
| 0 | 0 | 0 | 0 | 0 | 0 | 0 | 0 |
| 0 | 0 | 0 | 0 | 5 | 0 | 0 | 0 |
| 0 | 0 | 0 | 4 | 3 | 0 | 0 | 0 |
| 0 | 0 | 0 | 8 | 2 | 0 | 0 | 0 |
| 0 | 0 | 0 | 0 | 4 | 0 | 0 | 0 |
| 0 | 0 | 0 | 0 | 0 | 0 | 0 | 0 |
| 0 | 0 | 0 | 0 | 0 | 0 | 0 | 0 |

RANGE 9-1

FIG. 5A

| 0 | 0 | 201 | 178 | 90 | 184 | 205 | 0 |
|---|---|---|---|---|---|---|---|
| 0 | 202 | 122 | 88 | 82 | 95 | 133 | 210 |
| 191 | 182 | 76 | 30 | 5 | 51 | 129 | 208 |
| 198 | 143 | 23 | 4 | 3 | 21 | 106 | 183 |
| 201 | 142 | 38 | 8 | 2 | 22 | 78 | 141 |
| 0 | 192 | 75 | 11 | 4 | 35 | 111 | 183 |
| 0 | 0 | 204 | 69 | 45 | 35 | 177 | 0 |
| 0 | 0 | 0 | 199 | 80 | 159 | 0 | 0 |

FIG. 5B

| 0 | 0 | 200 | 100 | 0 | 100 | 200 | 0 |
|---|---|---|---|---|---|---|---|
| 0 | 200 | 100 | 0 | 0 | 0 | 100 | 200 |
| 100 | 100 | 0 | 0 | 0 | 0 | 100 | 200 |
| 100 | 100 | 0 | 0 | 0 | 0 | 100 | 100 |
| 200 | 100 | 0 | 0 | 0 | 0 | 0 | 100 |
| 0 | 100 | 0 | 0 | 0 | 0 | 100 | 100 |
| 0 | 0 | 200 | 0 | 0 | 0 | 100 | 0 |
| 0 | 0 | 0 | 100 | 0 | 100 | 0 | 0 |

RANGE 1,000-100

FIG. 5C

| 0 | 0 | 0 | 70 | 90 | 80 | 0 | 0 |
|---|---|---|---|---|---|---|---|
| 0 | 0 | 20 | 80 | 80 | 90 | 30 | 10 |
| 90 | 80 | 70 | 30 | 0 | 50 | 20 | 0 |
| 90 | 40 | 20 | 0 | 0 | 20 | 0 | 80 |
| 0 | 40 | 30 | 0 | 0 | 20 | 70 | 40 |
| 0 | 90 | 70 | 10 | 0 | 30 | 10 | 80 |
| 0 | 0 | 0 | 60 | 40 | 30 | 70 | 0 |
| 0 | 0 | 0 | 90 | 80 | 50 | 0 | 0 |

RANGE 99-10

FIG. 5D

| 0 | 0 | 1 | 8 | 0 | 4 | 5 | 0 |
|---|---|---|---|---|---|---|---|
| 0 | 2 | 2 | 8 | 2 | 5 | 3 | 0 |
| 1 | 2 | 6 | 0 | 5 | 1 | 9 | 8 |
| 8 | 3 | 3 | 4 | 3 | 1 | 6 | 3 |
| 1 | 2 | 8 | 8 | 2 | 2 | 8 | 1 |
| 0 | 2 | 5 | 1 | 4 | 5 | 1 | 3 |
| 0 | 0 | 4 | 9 | 5 | 5 | 7 | 0 |
| 0 | 0 | 0 | 9 | 0 | 9 | 0 | 0 |

RANGE 9-1

CHARGED PARTICLE BEAM TREATMENT APPARATUS

BACKGROUND

Technical Field

A certain embodiment of the present invention relates to a charged particle beam treatment apparatus.

Description of Related Art

In the related art, for example, a charged particle beam treatment apparatus is known which treats a patient by irradiating an affected site of the patient with a charged particle beam. In the charged particle beam treatment apparatus, the charged particle beam accelerated by an accelerator is used for scanning by a scanning electromagnet. Thereafter, the affected site of the patient is irradiated with the charged particle beam. The charged particle beam treatment apparatus adjusts scanning speed of the charged particle beam, thereby adjusting a dose of the charged particle beam for irradiating the affected site.

SUMMARY

According to an embodiment of the present invention, there is provided a charged particle beam treatment apparatus including an accelerator that emits a charged particle beam by accelerating a charged particle, an irradiation unit that irradiates an irradiation target body with the charged particle beam, a beam transport line that connects the accelerator and the irradiation unit to each other, and that transports the charged particle beam from the accelerator to the irradiation unit, and a control unit that controls the irradiation unit in irradiating the irradiation target body with the charged particle beam. In a case where the irradiation target body is virtually divided into a plurality of layers in an irradiation depth direction of the charged particle beam, the irradiation unit includes a scanning unit that scans each layer with the charged particle beam. After one layer is scanned and irradiated with the charged particle beam by using a first current value, the control unit controls the irradiation unit so as to scan and irradiate the one layer with the charged particle beam by using a second current value which is different from the first current value.

DETAILED DESCRIPTION

Here, the charged particle beam treatment apparatus as described above does not change a current value of a charged particle beam, and maintains the current value to be constant during irradiation of the charged particle beam. Therefore, the current value of the charged particle beam is set in accordance with a region requiring a lowest dose so that the region requiring the lowest dose is not irradiated with an excessive dose of the charged particle beam. Other regions are irradiated with the charged particle beam for a lengthened period of time (for example, decreasing scanning speed in a case of a raster scanning method, and lengthening a spot staying time in a case of a spot scanning method). In this method, a necessary dose is obtained.

However, in a case of the above-described treatment, a high dose region needs to be irradiated with the charged particle beam having a low current (low dose rate) for a long time. Consequently, the irradiation time is significantly lengthened, thereby causing a problem in that a time required for the treatment is lengthened.

It is desirable to provide a charged particle beam treatment apparatus which can shorten a time required for charged particle beam treatment.

In the charged particle beam treatment apparatus according to the embodiment of the present invention, the irradiation unit includes the scanning unit that scans one layer with the charged particle beam. After the one layer is irradiated and scanned with the charged particle beam by using the first current value, the control unit controls the irradiation unit so as to irradiate and scan the one layer with the charged particle beam by using the second current value which is different from the first current value. According to this configuration, the irradiation unit can irradiate a low dose region with the charged particle beam by setting a current value which is lower between the first current value and the second current value. On the other hand, the irradiation unit can irradiate a high dose region with the charged particle beam by setting a current value which is higher between the first current value and the second current value. In this way, each region can be irradiated with the charged particle beam by using the current value suitable for a dose of each region. In this manner, the irradiation unit can avoid the high dose region from being irradiated with the charged particle beam having the current value suitable for the low dose region for a long period of time. According to the above-described configuration, it is possible to shorten a time required for charged particle beam treatment.

In the charged particle beam treatment apparatus, the control unit may control the irradiation unit so that a second region scanned with the charged particle beam by using the second current value includes a region different from a first region scanned with the charged particle beam by using the first current value. In this case, the first region and the second region are regions which are entirely or partially different from each other. Therefore, the irradiation unit can irradiate different regions with the charged particle beams having different current values. Accordingly, compared to a case where the same place is irradiated with the charged particle beams having the different current values, it is easy to calculate an irradiation time.

In the charged particle beam treatment apparatus, the control unit may control the irradiation unit, based on a treatment plan map in which at least the first region and the second region are set at a predetermined position. In the treatment plan map, the first region and the second region may be set, based on dose distribution of the charged particle beam which is planned at the predetermined position. In this case, based on the dose distribution of the treatment plan map, the first region and the second region are set. Accordingly, each region can be easily set.

In the charged particle beam treatment apparatus, the control unit may control the irradiation unit, based on a first map and a second map which are prepared in accordance with dose distribution of the charged particle beam planned for the one layer. The first map and the second map may mutually have different dose ranges of the charged particle beam. The first map may set a first region scanned with the charged particle beam by using the first current value. The second map may set a second region scanned with the charged particle beam by using the second current value. In this case, based on the first map and the second map which have mutually different dose ranges, the first region and the second region are set. Accordingly, each region can be easily set.

According to an embodiment of the present invention, it is possible to shorten a time required for charged particle beam treatment.

Hereinafter, a charged particle beam treatment apparatus according to an embodiment of the present invention will be described with reference to the accompanying drawings. In describing the drawings, the same reference numerals will be given to the same elements, and repeated description will be omitted.

Figure 1:
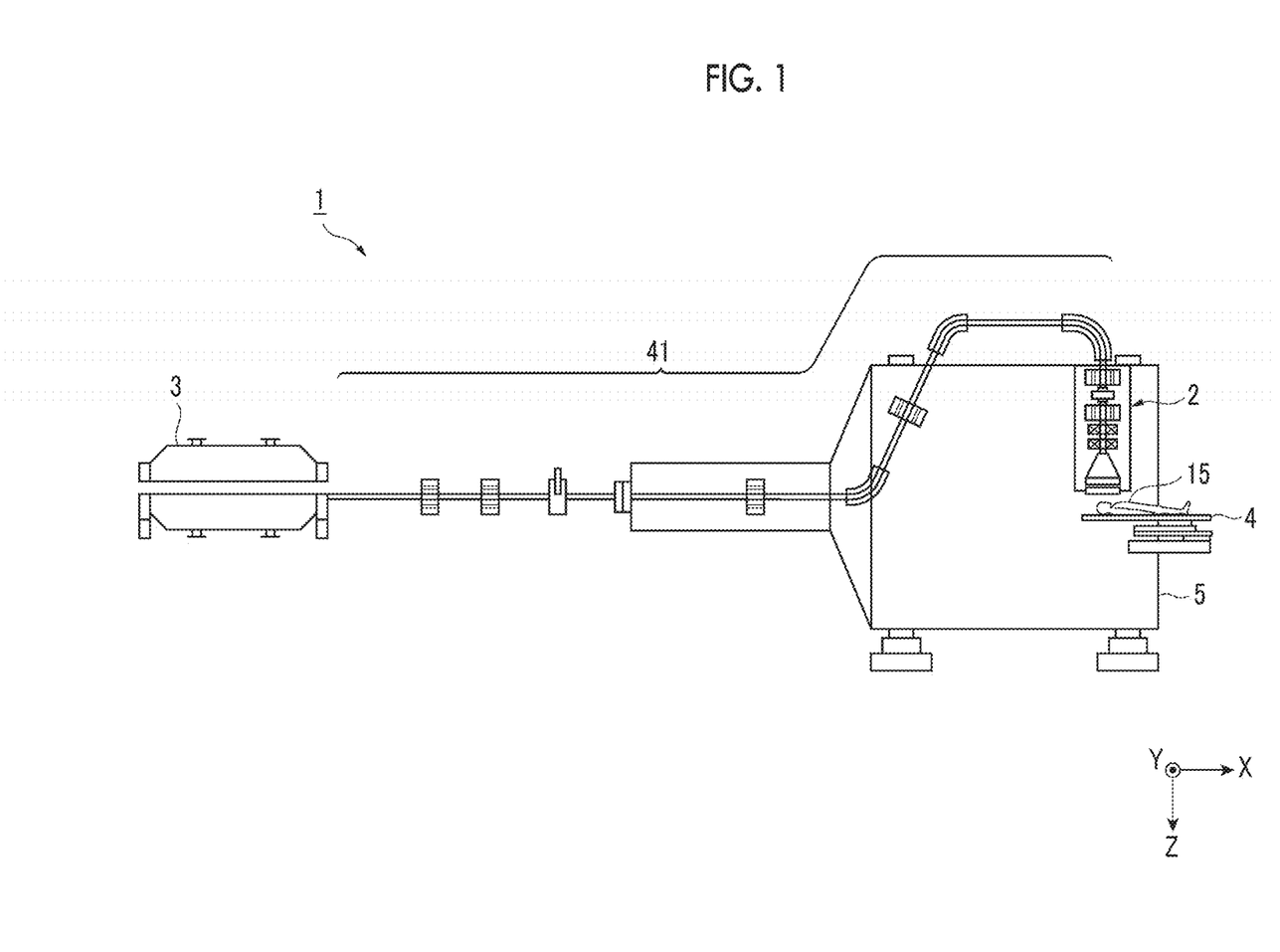
FIG. 1 is a perspective view of a charged particle beam treatment apparatus according to an embodiment of the present invention.

As illustrated in FIG. 1, a charged particle beam treatment apparatus 1 according to the embodiment of the present invention is used for cancer treatment using radiotherapy, and includes an accelerator 3 that emits a charged particle beam by accelerating a charged particle generated in an ion source (not illustrated), an irradiation unit 2 that irradiates an irradiation target body with the charged particle beam, and a beam transport line 41 that transports the charged particle beam emitted from the accelerator 3 to the irradiation unit 2. The irradiation unit 2 is attached to a rotary gantry 5 disposed so as to surround a treatment table 4. The irradiation unit 2 is rotatable around the treatment table 4 by the rotary gantry 5.

Figure 2:
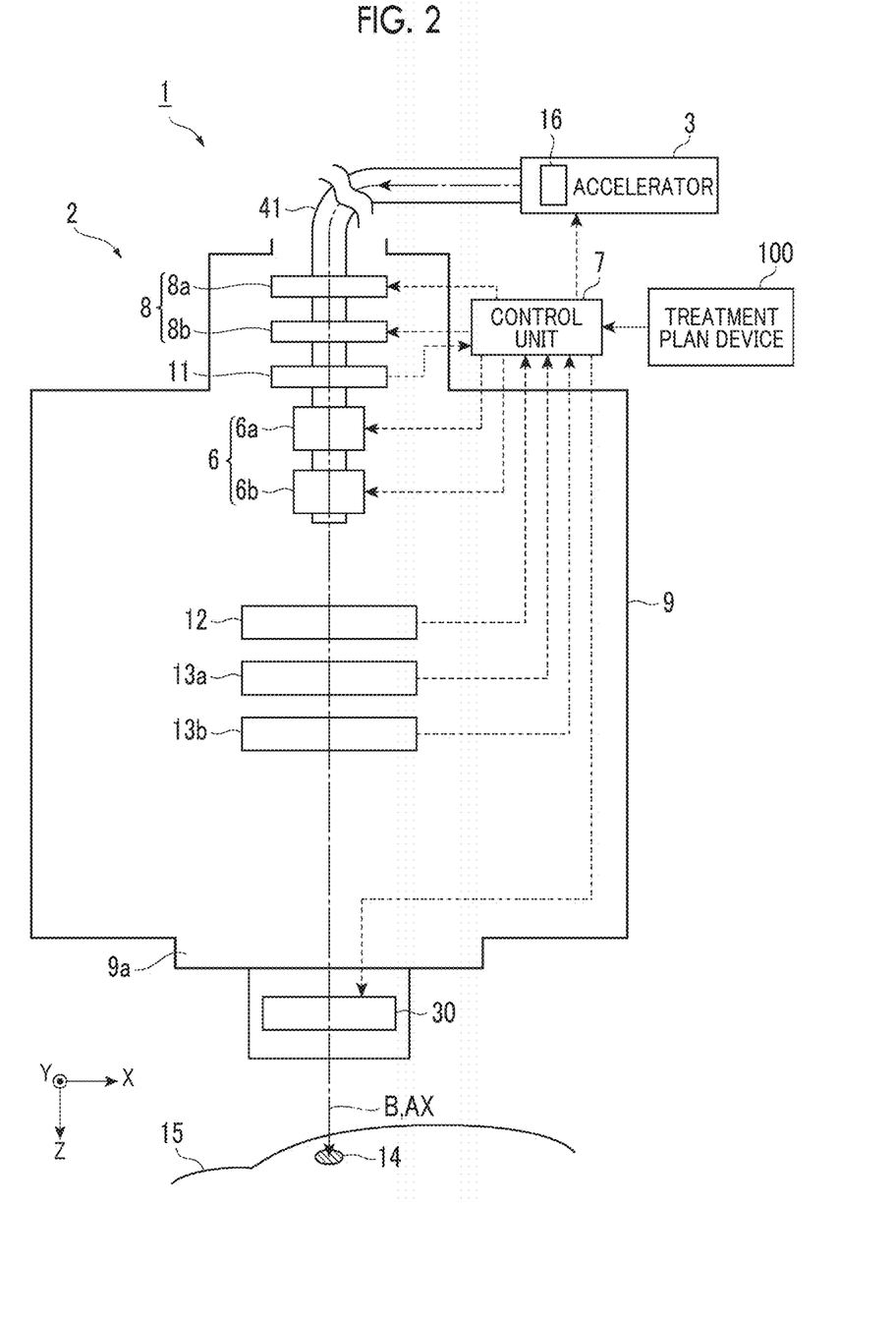
FIG. 2 is a schematic configuration diagram of an irradiation unit and a control unit of the charged particle beam treatment apparatus in FIG. 1.

FIG. 2 is a schematic configuration diagram of the irradiation unit and a control unit of the charged particle beam treatment apparatus in FIG. 1. In the following description, terms of an "X-direction", a "Y-direction" and a "Z-direction" will be used. The "Z-direction" is a direction in which a basic axis AX of a charged particle beam B extends, and is an irradiation depth direction of the charged particle beam B. The "basic axis AX" is an irradiation axis of the charged particle beam B in a case where the charged particle beam B is not deflected by a scanning electromagnet 6 (to be described later). FIG. 2 illustrates a state where an irradiation target is irradiated with the charged particle beam B along the basic axis AX. The "X-direction" is one direction in a plane orthogonal to the Z-direction. The "Y-direction" is a direction orthogonal to the X-direction in a plane orthogonal to the Z-direction.

First, referring to FIG. 2, a schematic configuration of the charged particle beam treatment apparatus 1 according to the present embodiment will be described. The charged particle beam treatment apparatus 1 is an irradiation apparatus relating to a scanning method. The scanning method is not particularly limited, and may employ line scanning, raster scanning, or spot scanning. As illustrated in FIG. 2, the charged particle beam treatment apparatus 1 includes the accelerator 3, the irradiation unit 2, the beam transport line 41, and the control unit 7.

The accelerator 3 is a device which accelerates the charged particle and emits the charged particle beam B. For example, accelerator 3 includes a cyclotron, a synchrotron, a synchrocyclotron, and a linear accelerator. The accelerator 3 is connected to the control unit 7, thereby controlling a current to be supplied. The charged particle beam B generated in the accelerator 3 is transported to an irradiation nozzle 9 by the beam transport line 41. The beam transport line 41 connects the accelerator 3 and the irradiation unit 2 to each other, and transports the charged particle beam emitted from the accelerator 3 to the irradiation unit 2.

The charged particle beam treatment apparatus 1 further includes a beam chopper 16 which is disposed inside the accelerator 3 and blocks the charged particle beam B emitted from an ion source. An operating state (ON) of the beam chopper 16 is a state where the charged particle beam B emitted from the ion source is blocked and not emitted from the accelerator 3. A stopped state (OFF) of the beam chopper 16 is a state where the charged particle beam B emitted from the ion source is emitted from the accelerator 3 without being blocked. The operating state and the stopped state of the beam chopper 16 are switched therebetween by a beam chopper switch (not illustrated). Other means for switching between irradiation and non-irradiation of the charged particle beam may be used instead of the beam chopper. For example, a shutter may be disposed in the beam transport line so that the shutter blocks the charged particle beam. Alternatively, only when an irradiation target is irradiated with the charged particle beam by using a deflector (electromagnet) disposed in the accelerator 3, the charged particle beam may be emitted from the accelerator 3.

The irradiation unit 2 irradiates a tumor (irradiation target body) 14 inside a body of a patient 15 with the charged particle beam B. The charged particle beam B is obtained by accelerating a charged particle at high speed, and includes a proton beam, a heavy particle (heavy ion) ray, or a particle beam, for example. Specifically, the irradiation unit 2 irradiates the tumor 14 with the charged particle beam B which is emitted from the accelerator 3 for accelerating the charged particle generated in the ion source (not illustrated) and which is transported by the beam transport line 41. The irradiation unit 2 includes a scanning electromagnet (scanning unit) 6, a quadrupole electromagnet 8, a profile monitor 11, a dose monitor 12, flatness monitors 13a and 13b, and a degrader 30. The scanning electromagnet 6, the respective monitors 11, 12, 13a, and 13b, the quadrupole electromagnet 8, and the degrader 30 are accommodated in the irradiation nozzle 9.

The scanning electromagnet 6 includes an X-direction scanning electromagnet 6a and a Y-direction scanning electromagnet 6b. The X-direction scanning electromagnet 6a and the Y-direction scanning electromagnet 6b are respectively configured to include a pair of electromagnets, and change a magnetic field between the pair of electromagnets in response to a current supplied from the control unit 7 so that the tumor 14 is scanned with the charged particle beam B passing between the electromagnets. The X-direction scanning electromagnet 6a uses the charged particle beam B for scanning in the X-direction, and the Y-direction scanning electromagnet 6b uses the charged particle beam B for scanning in the Y-direction. These scanning electromagnets 6 are arranged on the basic axis AX in this order on a downstream side of the charged particle beam B from the accelerator 3.

The quadrupole electromagnet 8 includes an X-direction quadrupole electromagnet 8a and a Y-direction quadrupole electromagnet 8b. The X-direction quadrupole electromagnet 8a and the Y-direction quadrupole electromagnet 8b narrow and converge the charged particle beam B in response to a current supplied from the control unit 7. The X-direction quadrupole electromagnet 8a converges the charged particle beam B in the X-direction, and the Y-direction quadrupole electromagnet 8b converges the charged particle beam B in the Y-direction. The current supplied to the quadrupole electromagnet 8 is changed, and the narrowing amount (convergence amount) is changed. In this manner, a beam size of the charged particle beam B can be changed. The quadrupole electromagnets 8 located on the basic axis AX in this order between the accelerator 3 and the scanning electromagnet 6. The beam size is a size of the charged particle beam B in an XY-plane. A beam shape (to be described later) is a shape of the charged particle beam B in the XY-plane.

The profile monitor 11 detects the beam shape and position of the charged particle beam B for alignment at the time of initial setting. The profile monitor 11 is located on the basic axis AX between the quadrupole electromagnet 8 and the scanning electromagnet 6. The dose monitor 12 detects the intensity of the charged particle beam B. The dose monitor 12 is located on the basic axis AX on the downstream side from the scanning electromagnet 6. The flatness monitors 13a and 13b detect and monitor the beam shape and position of the charged particle beam B. The flatness monitors 13a and 13b are located on the basic axis AX on the downstream side of the charged particle beam B from the dose monitor 12. The respective monitors 11, 12, 13a, and 13b output a detection result to the control unit 7.

The degrader 30 reduces the energy of the charged particle beam B passing therethrough, and adjusts an emitting range of the charged particle beam B. The emitting range is roughly adjusted by a degrader (not illustrated) disposed immediately after the accelerator 3, and is finely adjusted by the degrader 30 inside the irradiation nozzle 9. The degrader 30 is located on the basic axis AX on the downstream side of the charged particle beam B from the scanning electromagnet 6, and adjusts the maximum arrival depth of the charged particle beam B inside the body of the patient 15. In the present embodiment, the degrader 30 is disposed in a distal portion 9a of the irradiation nozzle 9. The distal portion 9a of the irradiation nozzle 9 is an end portion on the downstream side of the charged particle beam B. The degrader 30 inside the irradiation nozzle 9 can be omitted. In a case where the synchrotron is employed as the accelerator 3, the degrader disposed immediately after the accelerator 3 may be omitted. Instead of causing the degrader to adjust the energy of the charged particle beam after the charged particle beam is emitted from the accelerator 3, the energy of the charged particle beam emitted from the accelerator 3 may be adjusted.

For example, the control unit 7 is configured to include a CPU, a ROM, and a RAM. The control unit 7 controls the accelerator 3, the scanning electromagnet 6, and the quadrupole electromagnet 8, based on detection results output from the respective monitors 11, 12, 13a, and 13b. In the present embodiment, the control unit 7 feeds back the detection results of the respective monitors 11, 12, 13a, and 13b, and controls the quadrupole electromagnet 8 so that the charged particle beam B has a constant beam size.

The control unit 7 of the charged particle beam treatment apparatus 1 is connected to a treatment planning device 100 which carries out a treatment plan for charged particle beam treatment. Before the treatment, the treatment planning device 100 measures the tumor 14 of the patient 15 by using CT, and plans dose distribution (dose distribution of the charged particle beam to be used for irradiation) at each position of the tumor 14. Specifically, the treatment planning device 100 prepares a treatment plan map for the tumor 14. The treatment planning device 100 transmits the prepared treatment plan map to the control unit 7. Details of the treatment plan map will be described later.

In a case where the tumor 14 is irradiated with the charged particle beam by using a scanning method, the tumor 14 is virtually divided into a plurality of layers in the Z-direction, and the tumor 14 in one layer is scanned and irradiated with the charged particle beam. After the one layer is completely irradiated with the charged particle beam, the subsequent adjacent layer is irradiated with the charged particle beam.

In a case where the charged particle beam treatment apparatus 1 illustrated in FIG. 2 irradiates the tumor 14 with the charged particle beam B by using the scanning method, the degrader 30 is set which can adjust the charged particle beam B to have a predetermined emitting range. The quadrupole electromagnet 8 is brought into an operating state (ON) so as to converge the charged particle beam B passing therethrough.

Subsequently, the charged particle beam B is emitted from the accelerator 3. The emitted charged particle beam B is used for scanning under the control of the scanning electromagnet 6. In this manner, the tumor 14 is irradiated with the charged particle beam B while being used in scanning and irradiation within an irradiation range of the one layer set for the tumor 14 in the Z-direction. If the one layer is completely irradiated, a subsequent layer is irradiated with the charged particle beam B.

Figure 3A:
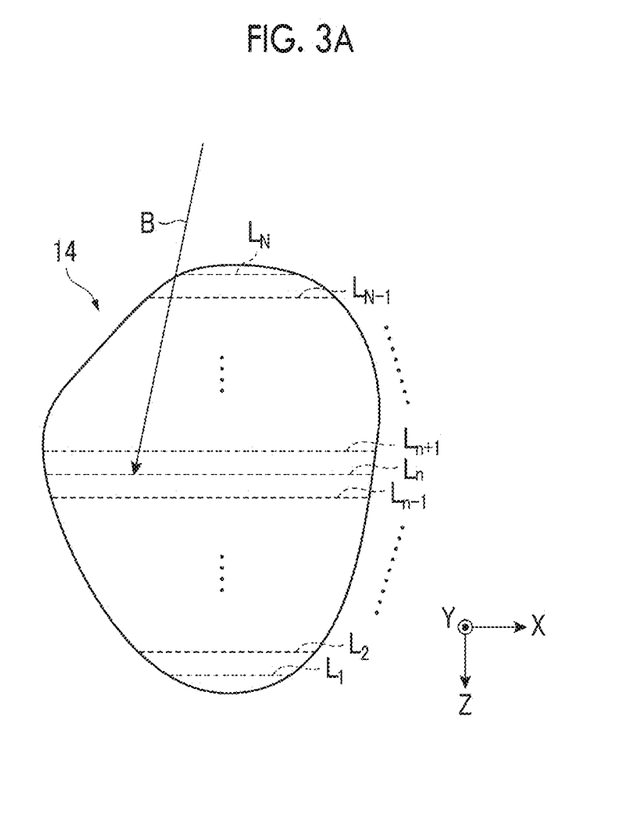
FIGS. 3A and 3B are views illustrating a layer set for a tumor.
Figure 3B:
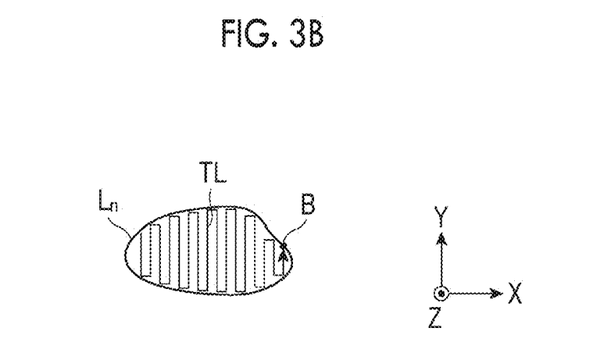

An irradiation image of the charged particle beam of the scanning electromagnet 6 in accordance with the control of the control unit 7 will be described with reference to FIGS. 3A and 3B. FIG. 3A illustrates an irradiation target body virtually sliced into the plurality of layers in the depth direction, and FIG. 3B illustrates a scanning image of the charged particle beam in one layer viewed in the depth direction.

As illustrated in FIG. 3A, the irradiation target body is virtually sliced into the plurality of layers in the irradiation depth direction. In this example, from the deepest layer (longest emitting range of the charged particle beam B), the irradiation target body is virtually sliced into Layers $L_1$, $L_2$, ..., Layer $L_{n-1}$, Layer $L_n$, Layer $L_{n+1}$, ..., Layer $L_{N-1}$, Layer $L_N$, and Layer N. As illustrated in FIG. 3B, a plurality of irradiation spots of Layer $L_n$ are irradiated with the charged particle beam B while the charged particle beam B draws a beam trajectory TL. That is, the irradiation nozzle 9 controlled by a scanning control unit 36 moves on the beam trajectory TL.

Next, an irradiation mode of the charged particle beam B used by the charged particle beam treatment apparatus 1 according to the present embodiment will be described. The control unit 7 irradiates and scans predetermined Layer $L_n$ with the charged particle beam B by using a first current value. Thereafter, the control unit 7 controls the irradiation unit 2 so that the predetermined Layer $L_n$ is irradiated and scanned with the charged particle beam B by using a second current value which is different from the first current value. The control unit 7 controls the irradiation unit 2 so that a second region to be scanned with the charged particle beam B by using the second current value includes a region different from the first region to be scanned with the charged particle beam B by using the first current value. The second region may partially overlap the first region, or may be located at a position completely different from that of the first region. As a result, the second region may completely overlap the first region.

Figure 6A:
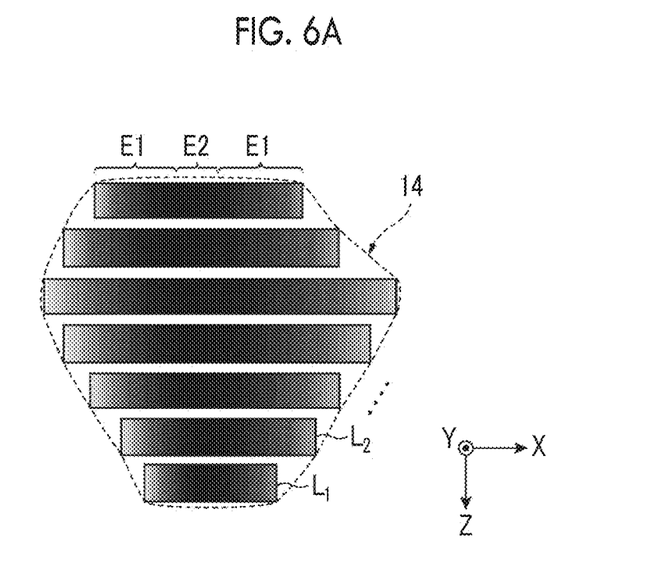
FIGS. 6A and 6B are schematic views illustrating dose distribution in each layer set for a tumor.
Figure 6B:
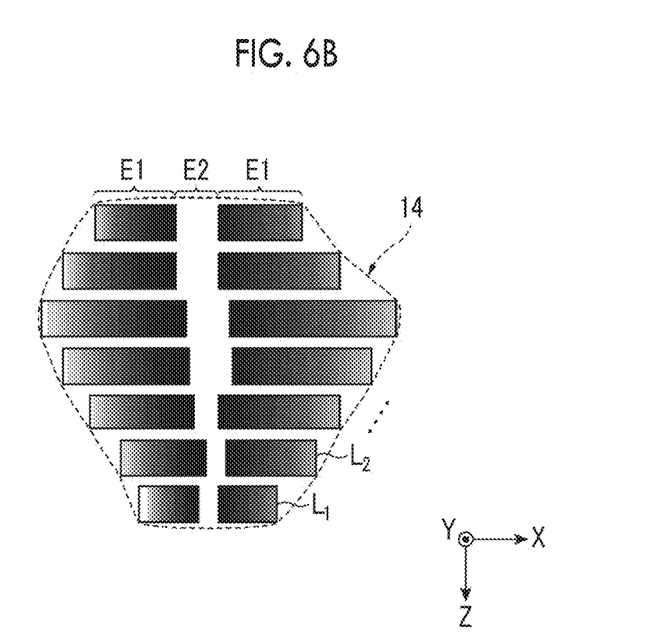

For example, a case will be described where the tumor 14 is irradiated with the charged particle beam B as illustrated in FIG. 6A. In FIG. 6A, the dose distribution for the predetermined Layer $L_n$ is indicated by color tints. A darker color region represents a low dose region, and a brighter color region represents a high dose region. For example, the high dose region exceeding a predetermined value is set as a first region E1, and the low dose region equal to or smaller than the predetermined value is set as a second region E2. In this case, as illustrated in FIG. 6B, in a case where the irradiation unit 2 irradiates the layer with the charged particle beam B by using the first current value (here, greater than the second current value), the irradiation unit 2 irradiates and scans only the first region E1 excluding the second region E 2 with the charged particle beam B. While the irradiation unit 2 irradiates the first region E1 with the charged particle beam B by using the first current value, and when the second region E2 is scanned with the charged particle beam B, the charged particle beam B is blocked by the beam chopper 16 (hereinafter, scanning in a state where the charged particle beam B is blocked in this manner is referred to as "idle driving"). In this manner, the second region E2 is not irradiated with the charged particle beam B. Thereafter, the irradiation unit 2 irradiates and scans the second region E2 with the charged particle beam B by using the second current value. Since the idle driving is not indispensable, the idle driving is performed if necessary. For example, in a case where another region is present in the middle of the beam scanning path, it is necessary to perform the idle driving on another region. On the other hand, in a case where another region is present on a terminal side of the scanning path, the idle driving is not performed, and the irradiation is completed when another region needs the irradiation.

The first region E1 of the predetermined Layer $L_n$ may be irradiated with the charged particle beam B by using the first current value, and thereafter, the second region E2 of the Layer $L_n$ may be irradiated with the charged particle beam B by using the second current value. Alternatively, the first region E1 of the predetermined Layer $L_n$ may be irradiated with the charged particle beam B by using the first current value, and thereafter, the first region E1 of the subsequent Layer Ln+1 (and layers subsequent thereto) may be irradiated with the charged particle beam B by using the first current value. After each layer is completely irradiated with the charged particle beam B by using the first current value, the second region E2 in each layer may be irradiated with the charged particle beam B by using the second current value.

Here, the control unit 7 may control the irradiation unit 2, based on the treatment plan map in which at least the first region and the second region are set for a predetermined layer. In the treatment plan map, the first region and the second region are set, based on the dose distribution of the charged particle beam B planned for a predetermined layer. That is, the control unit 7 can divide the dose distribution of the treatment plan map into predetermined ranges, and can set a region and a current value which correspond to each range. This calculation may be performed by the control unit 7 or by the treatment planning device 100.

Figure 4A:
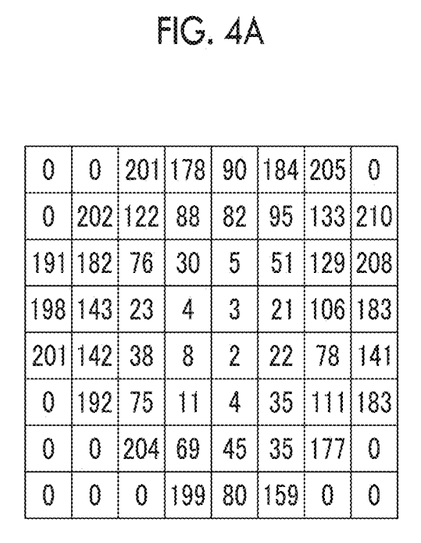
FIGS. 4A to 4D are views illustrating an example of a treatment plan map.
Figure 4B:
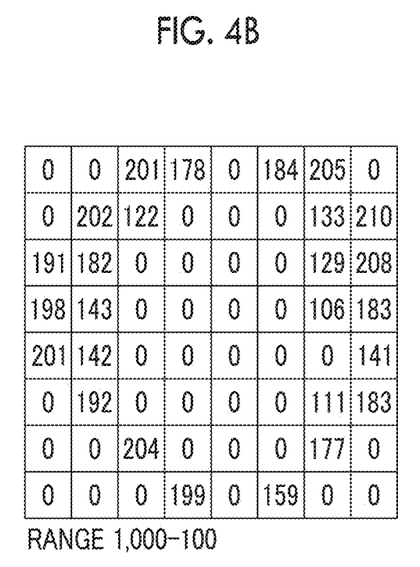
Figure 4C:
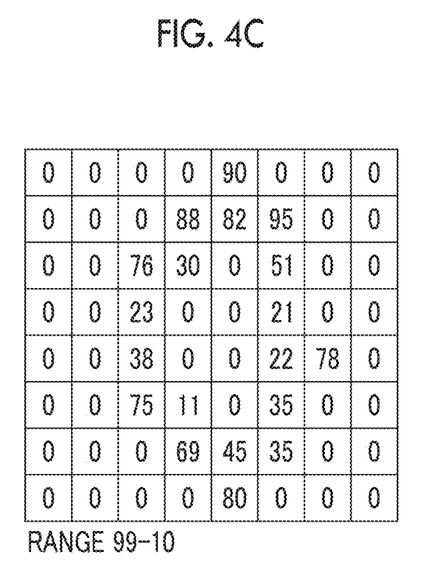
Figure 4D:
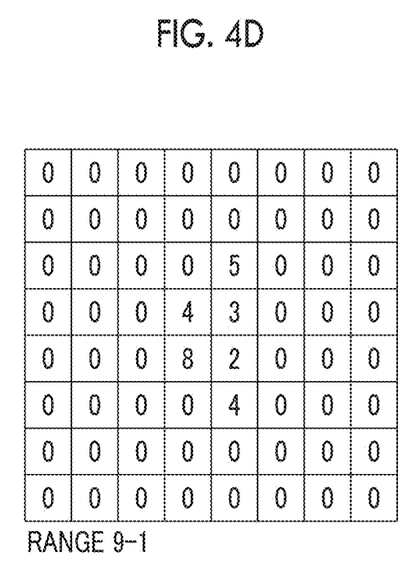

Specifically, in the treatment plan map, after the dose distribution illustrated in FIG. 4A is set, based on the strength of the dose distribution, a plurality of maps may be prepared which have mutually different dose ranges as illustrated in FIGS. 4B to 4D. For example, as illustrated in FIG. 4B, a map is prepared in which only the range whose dose is set to 1,000 to 100 is extracted in the treatment plan map of FIG. 4A. In this map, the extracted range (range whose dose is 1,000 to 100) is the first region to be irradiated with the charged particle beam B by using the first current value. In FIG. 4B, a place having numbers of 1,000 to 100 written thereon corresponds to the first region, and a place having "0" written thereon is the other region, which corresponds to a region on which the idle driving is performed (or a region which is not irradiated with charged particle beam). For the first region set in this way, the first current value is set in accordance with the smallest number among the numbers 1,000 to 100 (indicating a value of the dose). In the present embodiment, the first current value is set to a value (I[A]) corresponding to a dose 100. The control unit 7 irradiates each place of the first region with the charged particle beam B by adjusting an irradiation time in accordance with the number indicating the dose.

As illustrated in FIG. 4C, a map is prepared in which only the range whose dose is set to 99 to 10 is extracted in the treatment plan map of FIG. 4A. In this map, the extracted range (the range whose dose is set to 99 to 10) is the second region to be irradiated with the charged particle beam B by using the second current value. In FIG. 4C, a place having the numbers of 99 to 10 written thereon corresponds to the second region, and a place having "0" written thereon is the other region, which corresponds to a region on which the idle driving is performed (or a region which is not irradiated with charged particle beam). For the second region set in this manner, the second current value is set in accordance with the smallest number out of the digits 99 to 10 (indicating a value of the dose). In the present embodiment, the second current value is a value (I/10 [A]) corresponding to a dose 10. The control unit 7 irradiates each place of the second region with the charged particle beam B by adjusting the irradiation time in accordance with the number indicating the dose.

As illustrated in FIG. 4D, a map is prepared in which only the range whose dose is set to 9 to 1 is extracted in the treatment plan map of FIG. 4A. In this map, the extracted range (the range whose dose is set to 9 to 1) is the third region to be irradiated with the charged particle beam B by using the third current value. In FIG. 4D, a place having the numbers of 9 to 1 written thereon corresponds to the third region, and a place having "0" written thereon is the other region, which corresponds to a region on which the idle driving is performed (or a region which is not irradiated with charged particle beam). For the third region set in this way, the third current value is set in accordance with the smallest number among the numbers of 9 to 1 (indicating a value of the dose). In the present embodiment, the third current value is set to a value (I/100 [A]) corresponding to a dose 1. The control unit 7 irradiates each place of the third region with the charged particle beam B by adjusting the irradiation time in accordance with the number indicating the dose. However, since the dose in the third region is extremely smaller than that of the other region, the irradiation using the charged particle beam B may be omitted.

In the example illustrated in FIGS. 4A to 4D, three maps having mutually different dose ranges are prepared, based on the treatment plan map. The regions are irradiated with the charged particle beam B by using three different current values. However, two maps may be prepared so that the regions are irradiated with the charged particle beam B by using two different current values. Alternatively, four or more maps may be prepared so that the regions are irradiated with the charged particle beam B by using four or more different current values. In this case, the number of divided treatment plan maps may be set so that the irradiation is completed within a designated irradiation time. Although each map is prepared by dividing the map into ranges of 1,000 to 100, 99 to 10, and 9 to 1, a range corresponding to each map may be set to any range.

As described above, the first current value, the second current value, and the third current value are set as the current value. However, the irradiation order for each layer is not particularly limited, and may be set to an order which allows the shortest treatment time. A magnitude relationship between the respective current values is not particularly limited.

Next, an operation and an advantageous effect of the charged particle beam treatment apparatus 1 according to the present embodiment will be described.

In the charged particle beam treatment apparatus 1 according to the present embodiment, the irradiation unit 2 includes the scanning electromagnet 6 which uses the charged particle beam B in order to scan a predetermined layer (predetermined position) in the irradiation depth direction of the charged particle beam B. After the predetermined layer is irradiated and scanned with the charged particle beam B by using the first current value, the control unit 7 controls the irradiation unit 2 so as to irradiate and scan the predetermined region with the charged particle beam B by using the second current value which is different from the first current value. According to this configuration, the irradiation unit 2 can irradiate a low dose region with the charged particle beam B by setting the lower current value between the first current value and the second current value for the low dose region. On the other hand, the irradiation unit 2 can irradiate a high dose region with the charged particle beam B by setting the higher current value between the first current value and the second current value for the high dose region. In this way, each region can be irradiated with the charged particle beam by using the current value suitable for a dose in each region. In this manner, the irradiation unit 2 can avoid the high dose region from being irradiated with the charged particle beam having the current value suitable for the low dose region for a long period of time. According to the above-described configuration, it is possible to shorten a time required for the charged particle beam treatment.

For example, in the treatment plan map illustrated in FIG. 4A, in a case of irradiation using the related art, all regions are irradiated with the beam having the third current value (I/100[A]). Accordingly, if a time for irradiating the region with the dose 1 using the beam having the third current value is set to t-seconds, t×several thousand seconds are needed to irradiate all regions with the beam. In contrast, in the embodiment of the present invention, t×several tens of seconds are needed to irradiate the region indicated by the map in FIG. 4B by using the first current value, t×several tens of seconds are needed to irradiate the region indicated by the map in FIG. 4C by using the second current value, for, and t×several tens of seconds are needed to irradiate the region indicated by the map in FIG. 4D by using the third current value. Even in total, only t×several tens to hundreds of seconds are needed. Therefore, the irradiation time can be shortened to a level of 1/10 to 1/100.

In the charged particle beam treatment apparatus 1 according to the present embodiment, the control unit 7 controls the irradiation unit 2 so that the second region to be scanned with the charged particle beam B by using the second current value includes a region which is different from the first region to be scanned with the charged particle beam B by using the first current value. In this case, the first region and the second region are regions which are different from each other. Therefore, since the irradiation unit 2 can irradiate different regions with the charged particle beams having different current values. Accordingly, compared to a case where the same place is irradiated with the charged particle beam B having different current values, it becomes easy to calculate the irradiation time.

The control unit 7 controls the irradiation unit 2, based on the treatment plan map in which at least the first region and the second region are set for a predetermined layer (predetermined position). In the treatment plan map, the first region and the second region are set, based on the dose distribution of the charged particle beam B planned for the predetermined layer. In this case, the first region and the second region are set, based on the dose distribution of the treatment plan map. In this manner, each region can be easily set.

The control unit 7 controls the irradiation unit 2, based on the first map and the second map which are prepared in accordance with the dose distribution of the charged particle beam B planned for one layer. The first map and the second map have mutually different dose ranges of the charged particle beams. The first map sets the first region to be scanned with the charged particle beam B by using the first current value, and the second map sets the second region to be scanned with the charged particle beam B by using the second current value. In this case, the first region and the second region are set based on the first map and the second map which have mutually different dose ranges. In this manner, each region can be easily set.

The embodiment of the present invention is not limited to the above-described embodiment.

For example, in the embodiment described above (for example, a form using the treatment plan map of FIGS. 4A to 4D), the first region and the second region were set as completely different regions. Instead of this configuration, the first region and the second region may partially overlap each other. For example, all of the first region may be included in a portion of the second region. Alternatively, all of the second region may be included in a portion of the first region.

The configuration of the irradiation unit 2 is not limited to that illustrated in FIG. 2, and configurations other than at least the scanning electromagnet 6 may be appropriately changed.

Figure 5A:
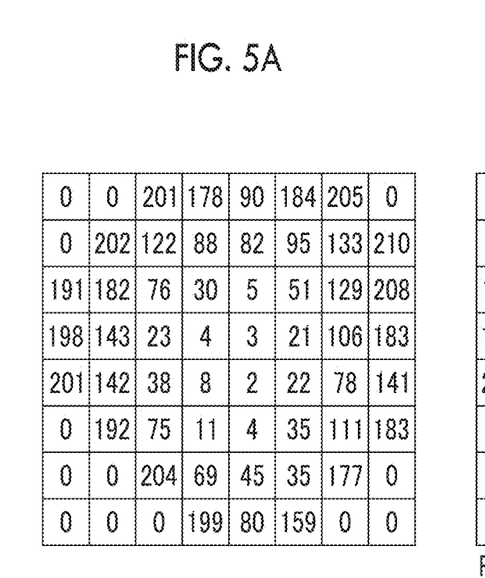
FIGS. 5A to 5D are views illustrating another example of the treatment plan map.
Figure 5B:
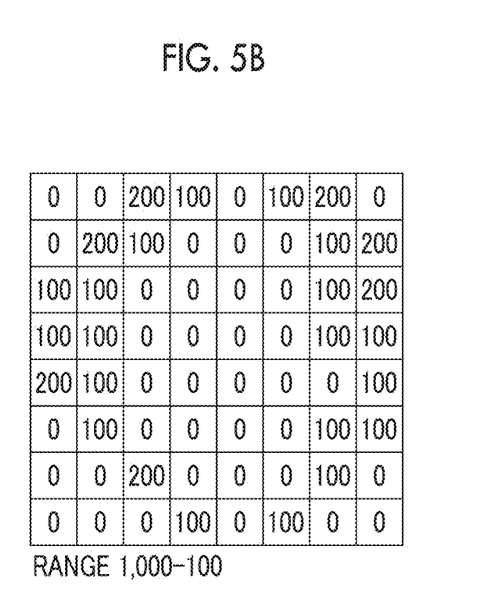
Figure 5C:
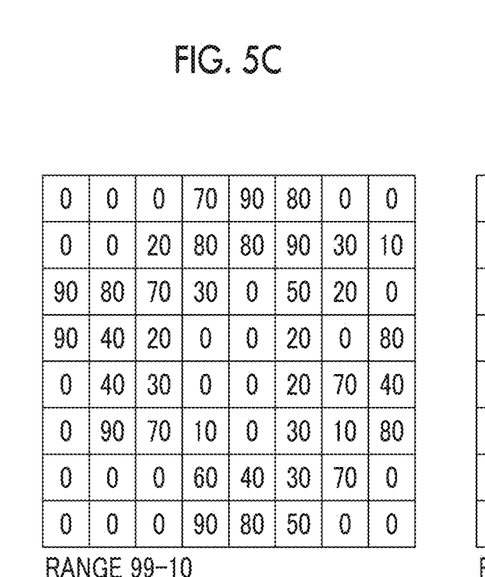
Figure 5D:
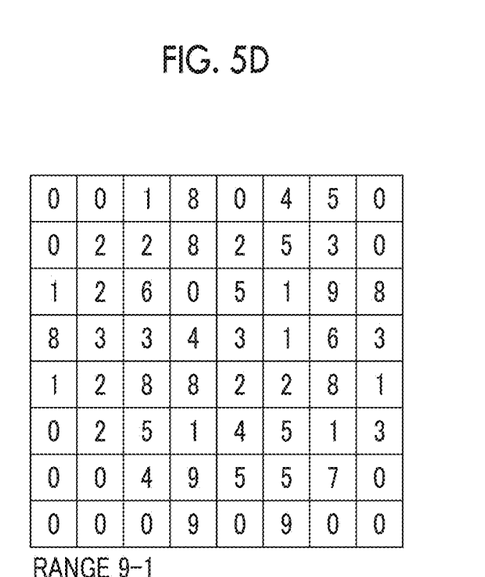

The maps corresponding to FIGS. 4B to 4D may be changed as illustrated in FIG. 5B to FIG. 5D. For example, in a case of the example of FIGS. 4A to 4D, numerical values of the tens place and the one place in the map of ranges 1,000 to 100 are rounded down. Therefore, as illustrated in FIGS. 5B to 5D, the dose value of each spot corresponding to the range is allocated. In this manner, it is possible to compatibly realize both shortened irradiation time and maintained irradiation accuracy.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus comprising:
    an accelerator configured to emit a charged particle beam by accelerating a charged particle;
    an irradiation unit configured to irradiate an irradiation target body with the charged particle beam;
    a beam transport line that connects the accelerator and the irradiation unit to each other, and configured to transport the charged particle beam from the accelerator to the irradiation unit; and a control unit configured to control the irradiation unit in irradiating the irradiation target body with the charged particle beam, wherein in a case where the irradiation target body is virtually divided into a plurality of layers in an irradiation depth direction of the charged particle beam, the irradiation unit includes a scanning unit configured to scan each layer with the charged particle beam, and wherein after all of one layer is scanned and a first region of the one layer is irradiated with the charged particle beam by using a first current value, the control unit controls the irradiation unit so as to scan all of the one layer and irradiate a second region of the one layer with the charged particle beam by using a second current value which is different from the first current value wherein the control unit controls the irradiation unit so that the second region irradiated with the charged particle beam by using the second current value includes a region different from the first region irradiated with the charged particle beam by using the first current value.

2. The charged particle beam treatment apparatus according to claim 1, wherein the control unit controls the irradiation unit, based on a treatment plan map in which at least the first region and the second region are set for the one layer, and wherein in the treatment plan map, the first region and the second region are set, based on dose distribution of the charged particle beam which is planned for the one layer.

3. The charged particle beam treatment apparatus according to claim 1, wherein the control unit controls the irradiation unit, based on a first map and a second map which are prepared in accordance with dose distribution of the charged particle beam planned for the one layer, wherein the first map and the second map mutually have different dose ranges of the charged particle beam, wherein the first map sets the first region irradiated with the charged particle beam by using the first current value, and wherein the second map sets the second region irradiated with the charged particle beam by using the second current value.

* * * * *